United States Patent [19]

Nukada et al.

[11] Patent Number: 5,495,049
[45] Date of Patent: Feb. 27, 1996

[54] TRIARYLAMINE COMPOUNDS USEFUL IN ELECTROPHOTOGRAPHIC PHOTORECEPTORS

[75] Inventors: Katsumi Nukada; Akira Imai; Ryosaku Igarashi, all of Minami Ashigara, Japan

[73] Assignee: Fuji Xerox Co., Ltd., Tokyo, Japan

[21] Appl. No.: 215,582

[22] Filed: Mar. 22, 1994

[30] Foreign Application Priority Data

Mar. 22, 1993 [JP] Japan .................. 5-085153
May 17, 1993 [JP] Japan .................. 5-136927
Jul. 7, 1993 [JP] Japan .................. 5-191821

[51] Int. Cl.$^6$ .................. C07C 211/54; C07C 211/60; C07C 211/61
[52] U.S. Cl. .................. 564/433; 564/435
[58] Field of Search .................. 564/433, 435

[56] References Cited

U.S. PATENT DOCUMENTS

| | | | |
|---|---|---|---|
| 3,180,730 | 4/1965 | Kluppel et al. | 96/1 |
| 3,706,554 | 12/1972 | Fox et al. | 96/1.6 |
| 4,946,754 | 8/1990 | Ong et al. | 430/59 |

FOREIGN PATENT DOCUMENTS

| | | |
|---|---|---|
| 57-195254 | 11/1982 | Japan . |
| 61-132953 | 6/1986 | Japan . |
| 1-280763 | 11/1989 | Japan . |
| 2-36156 | 2/1990 | Japan . |
| 2-156247 | 5/1990 | Japan . |
| 2-134642 | 5/1990 | Japan . |
| 2-178669 | 7/1990 | Japan . |
| 2-178666 | 7/1990 | Japan . |
| 2-178667 | 7/1990 | Japan . |
| 2-190862 | 7/1990 | Japan . |
| 2-190863 | 7/1990 | Japan . |
| 2-178670 | 7/1990 | Japan . |
| 2-178668 | 7/1990 | Japan . |
| 2-230255 | 9/1990 | Japan . |
| 2-243657 | 9/1990 | Japan . |
| 3-7248 | 1/1991 | Japan . |
| 3-7946 | 1/1991 | Japan . |
| 3-2174 | 1/1991 | Japan . |
| 3-5448 | 1/1991 | Japan . |
| 3-58054 | 3/1991 | Japan . |
| 3-56967 | 3/1991 | Japan . |
| 3-78756 | 4/1991 | Japan . |
| 3-78755 | 4/1991 | Japan . |
| 3-78757 | 4/1991 | Japan . |
| 3-101739 | 4/1991 | Japan . |
| 3-102361 | 4/1991 | Japan . |
| 3-114058 | 5/1991 | Japan . |
| 3-163458 | 7/1991 | Japan . |
| 3-213866 | 9/1991 | Japan . |
| 3-223764 | 10/1991 | Japan . |
| 3-249759 | 11/1991 | Japan . |
| 3-285960 | 12/1991 | Japan . |
| 3-282478 | 12/1991 | Japan . |
| 4-118658 | 4/1992 | Japan . |
| 4-133064 | 5/1992 | Japan . |
| 4-193852 | 7/1992 | Japan . |
| 5-16019 | 1/1993 | Japan . |
| 5-313386 | 11/1993 | Japan . |

OTHER PUBLICATIONS

Nukada et al., Chemical Abstracts, vol. 121 (1993) 69458.
Nukada et al., Chemical Abstracts, vol. 121 (1993) 46545.
Kanemaru et al., Chemical Abstracts, vol. 121 (1993) 22447.
Enomoto et al., Chemical Abstracts, vol. 118 (1991) 202023.
Karasawa et al., Chemical Abstracts, vol. 118 (1991) 29979.
Ueda et al., Chemical Abstracts, vol. 114 (1989) 256947.
Hanatani et al., Chemical Abstracts, vol. 113 (1988) 162507.
Kobayashi et al., Chemical Abstracts, vol. 111 (1987) 173733.
Hayes et al., Chemical Abstracts, vol. 93 (1980) 70833.
Parish, et al., Chemical Abstracts, vol. 62 (1964) 5211e.

*Primary Examiner*—Richard L. Raymond
*Attorney, Agent, or Firm*—Oliff & Berridge

[57] ABSTRACT

A triarylamine compound useful as a charge transport material of an electrophotographic photoreceptor, which represented by formula (I)

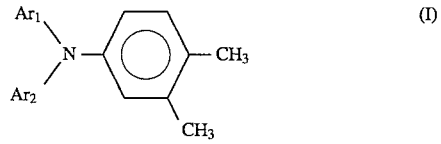

wherein $Ar_1$ and $Ar_2$ each represents a phenyl group or a condensed ring group.

5 Claims, 7 Drawing Sheets

TRIARYLAMINE COMPOUNDS USEFUL IN ELECTROPHOTOGRAPHIC PHOTORECEPTORS

FIELD OF THE INVENTION

The present invention relates to a novel triarylamine compound, a production process thereof and an electrophotographic photoreceptor using the triarylamine compound as a charge transport material.

BACKGROUND OF THE INVENTION

It is well known that a triarylamine compound is used as a charge transport material for an electrophotographic photoreceptor. For example, U.S. Pat. No. 3,180,730 discloses the use of triphenylamine and substituted products thereof as a charge transport material and U.S. Pat. No. 3,706,554 discloses the use of a tri-p-tolylamine compound. Also, JP-A-57-195254 (the term "JP-A" as used herein means an "unexamined published Japanese patent application") discloses the use of various triarylamine compounds in a charge tarnsport layer of a laminated layer type electrophotographic photoreceptor and further, JP-A-61-132953 discloses an electrophotographic photoreceptor using a trisazo pigment and a triarylamine compound in combination. Also, U.S. Pat. No. 4,946,754 discloses elecrtrophotographic photoreceptors using a diarylbiphenylamine and various charge generating materials.

Also, recently triarylamine compounds having various substituents are disclosed, for example, in JP-A-1-280763, JP-A-2-36156, JP-A-3-282478, JP-A-3-78755, JP-3-78756, JP-A-3-78757, JP-A-2-230255, JP-A-2-190862, JP-A-2-190863, JP-A-2-178670, JP-A-2-178668, JP-A-2-178667, JP-A-2-178666, JP-A-2-156247, JP-A-2-134642, JP-A-4-193852, JP-A-4-133064, JP-A-4-118658, JP-A-3-285960, JP-A-3-249759, JP-3-223764, JP-A-3-114058, JP-A-3-101739, JP-A-3-102361, JP-A-3-58054, JP-A-3-56967, JP-A-3-7946, JP-A-3-7248, JP-A-3-5448, JP-A-3-2174, JP-A-2-243657, JP-A-2-178669, JP-A-3-213866, JP-A-3-163458, etc.

Most typical triarylamine compounds are triphenylamine and tri-p-tolylamine and they are effective as a charge transport material for an electrophotographic photorecpetor. However, since these compounds have a small molecular weight and a low melting point, when an electrophotographic photoreceptor using the compound in a charge transport layer is repeatedly used, there are disadvantages that the compound causes a migration in the charge transport layer and also is liable to cause bleeding, whereby the characteristics of the electrophotographic photoreceptor are changed with the passage of time.

For eliminating the above-described defects, it is considered to incrase the molecular weight of the compound by introducing a substituent onto the compound. However, when a substituent not effective for transport of electrostatic charges is introduced, the distances between the molecules are increased to lower the mobility of electrostatic charges. The inventors found that an alkyl group is a substituent effective for transport of electrostatic charges, as described in Denshishashin Gakkai Shi (Journal of Electro-photographic Society.), Vol.30, 16(1990). However, when an alkyl group having a longer chain than an ethyl group is introduced, the compound is not liable to stack due to steric hindrance of the alkyl group, rather lowering the melting point, so that the compound tends to cause migration and a stable electrophotographic photoreceptor is not liable to obtain.

SUMMARY OF THE INVENTION

Accordingly, an object of the present invention is to provide a triarylamine compound free from the defects described above when used as a charge transport material in an electrophotographic photoreceptor.

Another object of the present invention is to provide a process of producing the triarylamine compound at a low cost.

A still another object of the present invention is to provide an electrophotographic photoreceptor having good stability.

As the result of intensive study, it has been found that by introduction of two methyl groups onto a phenyl group of triarylamine compounds, migration can be effectively prevented without lowering the melting point in contrast to introduction of a long chain alkyl group. It has also been found that a high charge mobility can be accomplished by adding the compound having two methyl groups at the 3- and 4- positions of the phenyl group in the charge transport layer of an electrophotographic photoreceptor and the electrophotographic photorecpetor is also excellent in stability upon repeated use.

The triarylamine compound of the present invention is represented by formula (I)

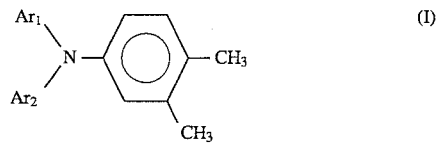

wherein, $Ar_1$ and $Ar_2$ each represents a phenyl group or a condensed ring group.

DETAILED DESCRIPTION OF THE INVENTION

Figure 1:
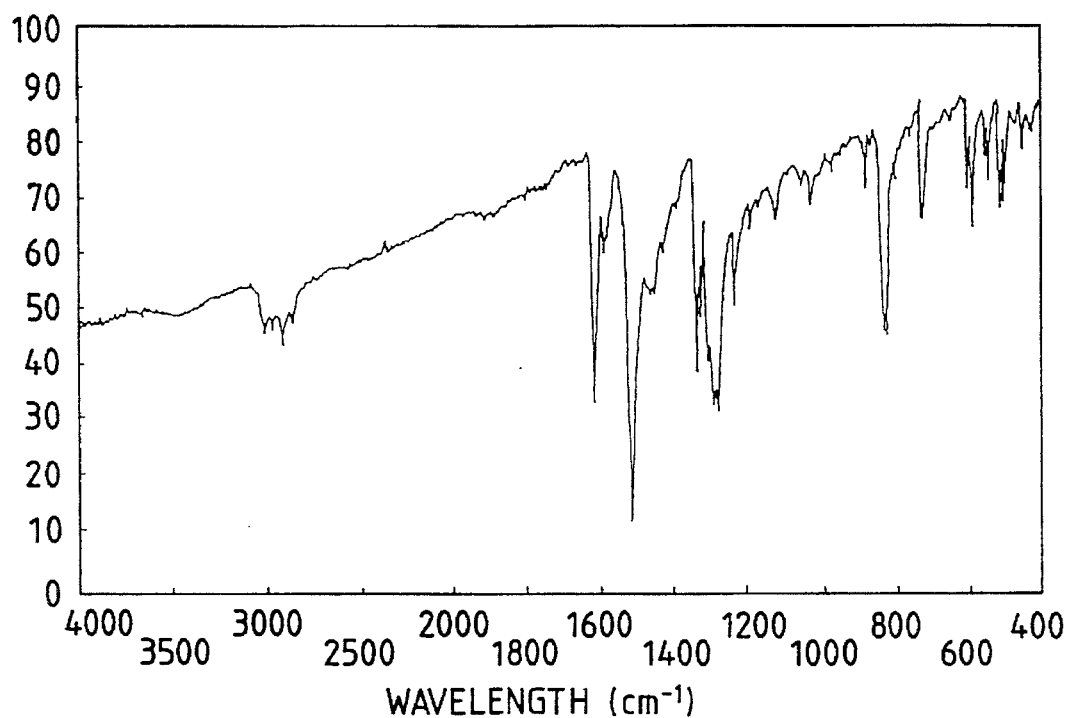
FIG. 1 to 14 are IR absorption spectra of the triphenylamine compounds prepared in Examples 1 to 14, respectively.

The triarylamine compound of the present invention can be synthesized by a condensation reaction of an amine and a halogenated aryl compound using a copper catalyst.

That is, the triarylamine compound of the present invention can be synthesized by acetylating 3,4-xylidine, thereafter condensing the acetylated product with a halogenated aryl compound of the $Ar_1$-X (wherein X represents a halogen atom and $Ar_1$ has the same meaning as described above) to form an N-(3,4-dimethylphenyl)-N-arylamine, and then condensing the diarylamine compound with a halogenated aryl compound of the formula $Ar_2$-X (wherein X represents a halogen atom and $Ar_2$ has the same meaning as described above).

Examples of the halogen in the halogenated aryl compound described above are bromine and iodine. In general, iodine is preferred since the reactivity is higher but bromine is preferred in the point of cost. In addition, in this case where 4-bromo-o-xylene is used as the halogenated aryl compound, 4-bromo-o-xylene can be used as an admixture with 3-bromo-o-xylene.

In detail, the acetylation of 3,4-xylidine can be conducted as follows. 3,4-xylidine is dissolved in an aqueous solution of hydrochloric acid, and then acetic anhydride and sodium acetate are successively added to the solution with stirring. The thus precipitated crystal is separated by filtration, fully washed with water and dried. If desired, purification of the product may be carried out, e.g., by way of recrystallization. The aqueous solution of hydrochloric acid may be a mixture of from 10 to 100 parts by weight (preferably from 15 to 50 parts by weight) and from 0.7 to 1.2 parts by weight (preferably from 0.8 to 1.0 part by weight) of concentrated hydrochloric acid, per part by weight of 3,4-xylidine.

Alternatively, 3,4-xylidine is added together with an organic solvent (e.g., n-hexane and toluene) to acetic anhydride with stirring. The reaction may be conducted under reflux if desired. After cooling the reaction mixture, the thus precipitated crystal is separated by filtration, fully washed with water and dried. Purification of the product may be carried out if desired. The amount of the organic solvent is generally from 2 to 20 parts by weight, preferably from 3 to 10 parts by weight, per part by weight of 3,4-xylidine.

The amounts of acetic anhydride and sodium acetate used for the above-described acetylation are not less than equivalent amount to that of 3,4-xylidine and preferably from 1.0 to 1.1 quivalents, respectively. The acetylation may be conducted at room temperature or may be conducted under a heated condition.

The two condensation reactions following the aforesaid acetylation may be a conventional coupling reaction of an amine and a halogenated aryl compound in the presence of a copper catalyst.

As the copper catalyst being used at the coupling reaction, there are a metallic copper powder, copper sulfate, cuprous oxide, copper iodide, copper nitrate, etc. The amount of the copper catalyst used can be selected depending upon the reaction rate. However, when the amount is too large, stirring of the reaction mixture and separation of the catalyst become difficult. The copper catalyst is generally used in an amount of 3 mols or less, and preferably 1 mol or less, per mol of the amine derivative. Also, hydrogen halide formed at the coupling reaction is neutralized by adding a base such as sodium carbonate, potassium carbonate, sodium hydroxide, potassium hydroxide, etc. The base is generally used in an amount of at least the equivalent amount to the amount of hydrogen halide generated but preferably not more than 10 equivalents, more preferably not more than 5 equivalents and particularly preferably from 0.1 to 5 equivalents. If the amount is too large, stirring, separation, etc. become difficult. Also, for removing water formed during the reaction from the reaction system, it is effective to carry out the reaction by adding a high-boiling hydrocarbon compound (e.g., tridecane and nitrobenzene) generally in an amount of from 0.01 to 10 parts by weight, preferably from 0.1 to 5 parts by weight, per part by weight of the amine derivative. The reaction temperature is generally from 150° to 300° C., preferably from 170° to 250° C., taking account of the heat durability of a reactor used.

A preferred production process of the present invention comprises acetylating an amino compound of the formula $Ar_1$-$NH_2$ (wherein $Ar_1$ has the same meaning as described above), carrying out a condensation reaction of the acetylated product with a mixture of 3-bromo-o-xylene and 4-bromo-o-xylene to form a diarylamine compound represented by formula (II)

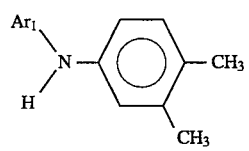

(wherein $Ar_1$ has the same meaning as described above), and then carrying out a condensation reaction of the diarylamine compound with a halogenated aryl compound of the formula $Ar_2$-$X_1$ (wherein $X_1$ represents a bromine atom or an iodine atom and $Ar_2$ has the same meaning as described above.).

In the condensation reaction after the acetylation 4-bromo-o-xylene is used for the introduction of the 3,4-xylyl group. However, since the purification of 4-bromo-o-xylene is difficult, an admixture with 3-bromo-o-xylene, which is easily avaliable, can be used advantageously. The mixture which can be practically used in the present invention contains at least 60% by weight, preferably from 70 to 80% by weight, of 4-bromo-o-xylene. 3-Bromo-o-xylene has a large steric hindrance due to the methyl group adjacent to the bromine atom and shows a very low reactivity as compared to 4-bromo-o-xylene, so that the desired 3,4-xylyl substituted product is mainly formed even using the admixture. Also, the 3,4-xylyl substututed product can be easily separated from the undesired 2,3-xylyl substituted product by utilizing the difference in solubility, for example, by recrystallization from an organic solvent such as methanol, ethanol, and hexanol.

The phenyl group represented by $Ar_1$ and $Ar_2$ in formula (I) may be substituted with an alkyl group preferably having 1 to 5 carbon atoms, an alkoxy group preferably having 1 to 5 carbon atoms, a phenyl group, or an alkyl(preferably $C_{1-5}$)-substituted phenyl group. The phenyl group for $Ar_1$ and $Ar_2$ may have plurality of these substituents. The condensed ring group of $Ar_1$ and $Ar_2$ includes a naphthyl group, an anthracenyl group, a pyrenyl group, a fluorenyl group, etc., which may be substituted with an alkyl group preferably having 1 to 5 carbon atoms.

Typical examples of the triarylamine compound of the present invention are illustrated in Table shown below. In the table, Me, Et, Pr, and Bu mean a methyl group, an ethyl group, a propyl group, and a propyl group, respectively.

TABLE 1

| | $Ar_1$ | $Ar_2$ |
|---|---|---|
| CT-1 | —Ph | —Ph |
| CT-2 | —Ph—Me | —Ph |
| CT-3 | —Ph—Me | —Ph—Me |
| CT-4 | —Ph—Me | —Ph—Ph |
| CT-5 | —Ph—Me | —Ph—Ph—Me |
| CT-6 | —Ph—Me | —(naphthyl) |

TABLE 1-continued

| | Ar₁ | Ar₂ |
|---|---|---|
| CT-7 | –⟨Ph⟩–Me | 9,9-dimethylfluorenyl |
| CT-8 | –⟨Ph⟩–Me | naphthyl |
| CT-9 | –⟨Ph⟩–Me | methylnaphthyl |
| CT-10 | –⟨Ph⟩–Me | methylnaphthyl |
| CT-11 | –⟨Ph⟩–Me | methylnaphthyl |
| CT-12 | 3,4-dimethylphenyl | –⟨Ph⟩ |
| CT-13 | 3,4-dimethylphenyl | –⟨Ph⟩–Me |
| CT-14 | 3,4-dimethylphenyl | biphenyl |
| CT-15 | 3,4-dimethylphenyl | –⟨Ph⟩–⟨Ph⟩–Me |
| CT-16 | 3,4-dimethylphenyl | methylpyrenyl |
| CT-17 | 3,4-dimethylphenyl | 9,9-dimethylfluorenyl |
| CT-18 | 3,4-dimethylphenyl | naphthyl |
| CT-19 | 3,4-dimethylphenyl | methylnaphthyl |
| CT-20 | 3,4-dimethylphenyl | methylnaphthyl |
| CT-21 | 3,4-dimethylphenyl | methylnaphthyl |
| CT-22 | 3,4-dimethylphenyl | –⟨Ph⟩–Et |
| CT-23 | 3,4-dimethylphenyl | –⟨Ph⟩–Pr |
| CT-24 | 3,4-dimethylphenyl | –⟨Ph⟩–i-Pr |
| CT-25 | 3,4-dimethylphenyl | 3,4-dimethylphenyl |
| CT-26 | –⟨Ph⟩–Me | –⟨Ph⟩–t-Bu |
| CT-27 | –⟨Ph⟩–t-Bu | –⟨Ph⟩–t-Bu |
| CT-28 | –⟨Ph⟩–t-Bu | biphenyl |
| CT-29 | –⟨Ph⟩–OMe | biphenyl |
| CT-30 | 3-methoxyphenyl | biphenyl |
| CT-31 | 3,4-dimethylphenyl | –⟨Ph⟩–t-Bu |
| CT-32 | 2,3-dimethylphenyl | biphenyl |
| CT-33 | biphenyl | biphenyl |
| CT-34 | biphenyl | methylnaphthyl |

The triarylamine compound of the present invention can be added as a charge transport material in a photosensitive layer of an electrophotographic photoreceptor. The photosensitive layer may have a single layer structure or a functionally separated laminate structure which comprises a charge generating layer and a charge tansport layer, with the laminate type photosensitive layer being preferred. In the case of the single layer type photosensitive layer, the triarylamine compound is contained in the layer together with a charge generating material. In the case of the laminate type photosensitive layer, the triarylamine compound is added to the charge transport layer. For example, in an electrophotographic photoreceptor comprising an electrically conductive support such as aluminum, etc., having formed thereon a charge generating layer and a charge transport layer, the foregoing triarylamine compound of the present invention is contained in the charge transport layer.

More practically, the charge transport layer may be formed by coating a coating liquid containing the triarylamine compound of the present invention and a resin binder.

As the binder resin, known resins such as a polycarbonate resin, a polyester resin, a methacrylic resin, an acrylic resin, a polyvinyl chloride resin, a polyvinylidene chloride resin, a polystyrene resin, a polyvinyl acetate resin, a styrene-butadiene copolymer, a vinylidene chloride-vinyl acetate-maleic anhydride copolymer, a silicone resin, a silicone-alkyd resin, a phenol-formaldehyde resin, a styrene-alkyd resin, poly-N-vinylcarbazole, polysilane, etc., can be used. Of these, polycarbonate resins shown by formulae (III) to (VII), or polycarbonate resins obtained by copolymerization thereof are preferred since these resins have a good compatibility with the triarylamine compound to form a uniform layer and the resulting electrophotographic photoreceptors exhibit particularly good characteristics.

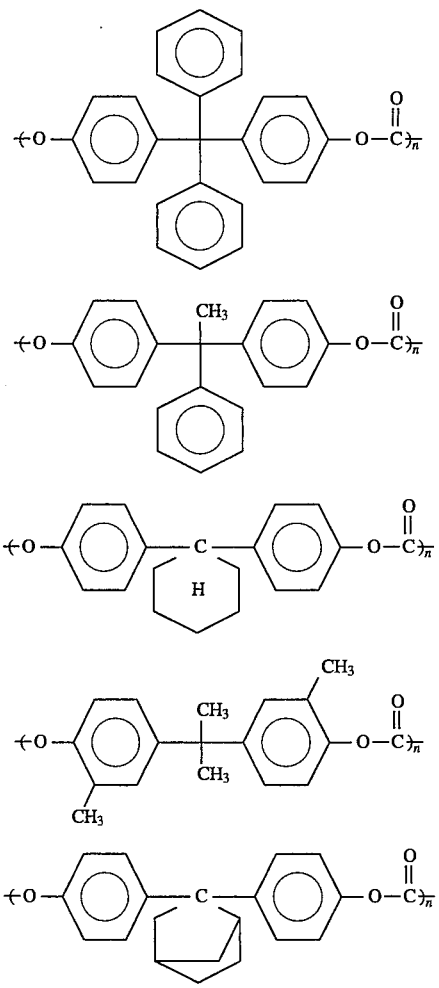

The binder resins can be used singly or as a mixture thereof.

The compounding ratio (weight ratio) of the charge transport material to the binder resin is preferable from 10/1 to 1/5.

The photosensitive layer of the electrophotographic photoreceptor preferably contains as a charge generating material at least one compound selected from the group consisting of halogenated gallium phthalocyanine crystals, halogenated tin phthalocyanine crystals, hydroxygallium phthalocyanine crystals, and titanyl phthalocyanine crystals.

Examples of halogenated gallium phthalocyanine crystals include a chlorogallium phthalocyanine crystal showing at least distinct diffraction peaks at Bragg angles ($2\theta \pm 0.2°$) of 7.4°, 16.6°, 25.5°, and 28.3° in an X-ray diffraction spectrum using $CuK_\alpha$ as a radiation source (hereafter merely describing in parenthesis the Bragg angles at which distinct diffraction peaks are observed), a chlorogallium phthalocyanine crystal (6.8°, 17.3°, 23.6°, and 26.9°), and a chlorogallium phthalocyanine crystal (8.7°–9.2°, 17.6°, 24.0°, 27.4°, and 28.8°)

Examples of halogenated tin phthalocyanine crystals include a dichlorotin Phthalocyanine crystal (8.5°, 11.2°, 14.5°, and 27.2°), a dichlorotin phthalocyanine crystal (8.7°, 9.9°, 10.9°, 13.1°, 15.2°, 16.3°, 17.4°, 21.9°, and 25.5°), and a dichlorotin phthalocyanine crystal (9.2°, 12.2°, 13.4°, 14.6°, 17.0°, and 25.3°).

Examples of hydroxygallium phthalocyanine crystals include a crystal (7.7°, 16.5°, 25.1°, and 26.20 ), a crystal (7.9°, 16.5°, 24.4°, and 27.6°), a crystal (7.0°, 7.5°, 10.5°, 11.7°, 12.7°,17.3°, 18.1°, 24.5°, 26.2°, and 27.°), a crystal (7.5°, 9.9°, 12.5°, 16.3°, 18.6°, 25.1°, and 28.3°), a crystal (6.8°, 12.8°, 15.8°, and 26.0°), a crystal (7.4°, 9.9°, 25.0°, 26.2°, and 28.2°), a crystal (8.2°, 12.4°, 16.5°, and 126.3°), and a crystal (6.8°, 12.5°, and 26.4°).

Examples of titanyl phthalocyanine crystals include a crystal (27.3°) which comes to have a structure represented by the formula $TiOPc(H_2O)_n$ (wherein Pc represents a phthalocyanine residue, and n is a real number of 0.15 to 1) and to show the data of elemental analysis of C: 65.0 to 66.3 , H: 2.5 to 3.1, and N: 18.5 to 19.3% when dried at 100° C. for 8 hours under reduced pressure of 0.1 mmHg, followed by allowing to stand for 12 hours under atmospheric conditions, a crystal (9.2°, 13.1°, 20.7°, 26.2°, and 27.1°), and a crystal (7.6°, 12.3°, 16.3°, 25.3°, and 28.7°).

All the phthalocyanine crystals as exemplified above have novel crystal forms and they can be synthesized in the following manner. The novel crystal chlorogallium phthalocyanines can be produced by a wet-grinding treatment of chlorogallium phthalocyanine crystals as prepared by known methods, with an automortar, a planet mill, an oscillating mill, a CF mill, a roll mill, a sand mill, a kneader and the like. The wet-grinding treatment is carried out using a solvent such as aromatic solvents (e.g., toluene and monochlorobenzene), amides (e.g., dimethylformamide and N-methyl-pyrrodone), aliphatic alcohols (e.g., methanol, ethanol, and butanol), aliphatic polydydric alcohols (e.g., ethylene glycol, glycerol, and polyethylene glycol), aromatic alcohols (e.g., benzyl alcohol and phenethyl alcohol), esters (e.g., ethyl acetate and butyl acetate), ketones (e.g., acetone and methyl ethyl ketone), dimethylsulfoxide, and ethers (e.g., diethyl ether and tetrahydrofuran). The solvent may be used independently or as a mixture of two or more thereof and may also be used as admixture with water. The solvent is generally used in an amount of from 1 to 200 parts by weight, preferably from 10 to 100 parts by weight, per part by weight of chlorogallium phthalocyamine. The wet-grinding treatment is generally conducted at a temperature of from 0° C. to less than the boiling point of a solvent used and preferably from 10° to 60° C. Grinding aids such as common salt and Glauber's salt may be added, during grinding, in an amount of from 0.5 to 20 parts by weight, preferably from 1 to 10 parts by weight, per part by weight of chlorogallium phthalocyamine.

The novel crystal dichlorotin phthalocyanines can be produced by a wet-grinding treatment of dichlorotin phthalocyanine crystals as prepared by known methods, in the same manner as described above.

The novel crystal hydroxygallium phthalocyanines can be produced in the following manner. Chlorogallium phthaloanine crystals prepared by known methods are subjected to hydrolysis in an acidic or alkaline solution or to an acid-pasting treatment, to thereby synthesize hydroxygallium phthalocyanine crystals which are then subjected to a solvent treatment, a wet-grinding treatment in the presence of a solvent using a ball mill, a mortar, a sand mill, a kneader or the like, or a dry-grinding treatment followed by a solvent treatment.

The solvent as used in the above processings can be exemplified with those described in production of the novel crystal chlorogallium phthalocyanines. The solvent is generally used in an amount of form 1 to 200 parts by weight, preferably form 10 to 100 parts by weight, per part by weight of hydroxygallium phthalocyanine crystal. The solvent treatment is generally conducted at a temperature of from 0° to 150° C. and preferably from room temperature to 100° C. During the wet- or dry-grinding, grinding aids may also be used as in production of the novel crystal chlorogallium phthalocyanines.

The novel crystal titanyl phthalocyanines can be produced in the following manner. Titanyl phthalocyanine crystals as prepared by known methods are subjected to an acid-pasting treatment, or a salt-milling with an inorganic salt in a ball mill, a mortar, a sand mill, a kneader or the like, to obtain titanyl phthalocyanine crystals having a low-crystallinity which are then subjected to a solvent treatment or a wet-grinding treatment in the presence of a solvent using a ball mill, a mortal, a sand mill, a kneader or the like.

The acid-pasting treatment is preferably conducted using a sulfuric acid, a concentration of which is from 70 to 100% and preferably from 95 to 100%, at a temperature of from −20° to 100° C. and preferably from 0° to 60° C. The amount of the concentrated sulfuric acid is generally from 1 to 100 parts by weight, preferably from 3 to 50 parts by weight, per part by weight of the titanyl phthalocyanine crystal. The thus formed low-crystallinity titanyl phthalocyanine crystals are precipitated from water or a mixed solvent of water and an organic solvent. In particular, a mixed solvent of water and an alcoholic solvent (e.g., methanol and ethanol) and a mixed solvent of water and an aromatic solvent (e.g., benzene and toluene) are preferably used for the purpose. The precipitation temperature is not particularly limited, but precipitation is preferably conducted with ice-cooling so as to prevent an adverse influence of exothermic heat.

In the salt-milling treatment, the weight ratio of the titanyl phthalocyamine crystals to an inorganic salt is generally from 1/0.1 to 1/20 and preferably from 1/0.5 to 1/5.

Examples of the solvent which can be used in the treatment of low-crystallinity titanyl phthalocyanine crystals include aromatic solvents (e.g., toluene and monochlorobenzene), aliphatic alcohols (e.g., methanol, ethanol, and butanol), and halogenated hydrocarbons (e.g., dichloromethane, chloroform, and trichloroethane), which may be used independently or as a mixture thereof, with or without water. The solvent is generally used in an amount of from 1 to 10 parts by weight, preferably from 5 to 50 parts by weight, per part by weight of titanyl phthalocyanine. The solvent treatment is conducted at a temperature of from room temperature to 100° C. and preferably from 50° to 100° C. During the wet-grinding treatment, grinding aids may be added in an amount of from 0.5 to 20 parts by weight, preferably from 1 to 10 parts by weight, per part by weight of titanyl phthalocyanine.

Synthesis of the phthalocyanine crystals which are preferably used as a charge generating material in a photosensitive layer are explained with reference to Synthesis Examples below. In the Synthesis Example, all parts are by weight.

Synthesis Example 1

Synthesis of chlorogallium phthalocyanine crystals:

(i) To 230 parts of quinoline were added 30 parts of 1,3-diiminoisoindoline and 9.1 parts of gallium trichloride, and they were reacted at 200° C. for 3 hours. The reaction product was obtained by filtration and washed with acetone and methanol, followed by drying, whereby 28 parts of chlorogallium phthalocyanine crystals were obtained.

(ii) 3 parts of the thus obtained chlorogallium phthalocyamine crystals were subjected to dry-grinding for 3 hours using an automortar ("Lab-Mill UT-21 Type", manufactured by Yamato Kagaku K.K.). 0.5 part of the ground crystals were milled with 60 parts of glass beads (diameter: 1 mm) in 20 parts of benzyl alcohol at room temperature for 24 hours. After removing the glass beads, the residue was washed with 10 parts of methanol and dried to obtain a chlorogallium phthalocyanine crystal (CG-1) showing at least distinct diffraction peaks at Bragg angles ($2\theta \pm 0.2°$) of 7.4°, 16.6°, 25.5° and 28.3° in X-ray diffraction spectrum using $CuK_\alpha$ as a radiation source.

The same treatments as described above were repeated except for using methylene chloride or methanol in place of benzyl alcohol to obtain a chlorogallium phthalocyamine crystal (CG-2) showing distinct diffraction peaks at Bragg angles ($2\theta \pm 0.2°$) of 6.8°, 17.3°, 23.6°, and 26.9°, or a chlorogallium phthalocyanine crystal (CG-3) showing distinct diffraction peaks at Bragg angles ($2\theta \pm 0.2°$) of 8.7°–9.2°, 17.6°, 24.0°, 27.4°, and 28.8°, respectively.

Synthesis Example 2

Synthesis of dichlorotin phthalocyanine crystals:

(i) To 350 ml of 1-chloronaphthalene were added 50 g of phthalonitrile and 27 g of anhydrous stannic acid, and they were reacted at 195° C. for 5 hours. The reaction products were separated by filtration and washed subsequently with 1-chloronaphthalene, acetone, methanol and then water. After drying under reduced pressure, 18.3 g of dichlorotin phthalocyanine crystals were obtained.

(ii) 5 g of the thus obtained crystals were placed in a pot made of agate together with 10 g of common salt and 50 g of agate balls (diameter: 20 mm) and they were ground with a planet ball mill ("P-5 Type", manufactured by Fritchu Co.) at 400 rpm for 10 hours. The resultant was thoroughly washed with water and dried. 0.5 part of the ground crystals was milled with 15 g of tetrahydrofuran and 30 g of glass beads (diameter: 1 mm) at room temperature for 24 hours. After removing the glass beads, the residue was washed with methanol and dried, whereby a dichlorotin phthalocyanine crystal (CG-4) showing distinct diffraction peaks at Bragg angles ($2\theta \pm 0.2°$) of 8.5°, 11.2°, 14.5°, and 27.2° was obtained.

The same treatment as described above were repeated except for using monochlorobenzene in place of tetrahydrofuran, or changing the milling time of 24 hours to 60 hours, to thereby obtain a dichlorotin phthalocyanine crystal (CG-5) showing distinct diffraction peaks at Bragg angles ($2\theta \pm 0.2°$) of 8.7°, 9.9°, 10.9°, 13.1°, 15.2°, 16.3°, 17.4°, 21.9°, and 25.5°, or a dichlorotin phthalocyanine crystal (CG-6) showing distinct diffraction peaks at Bragg angles (2θ±0.2°) of 9.2°, 12.2°, 13.4°, 14.6°, 17.0°, and 25.3°.

Synthesis Example 3

Synthesis of hydroxygallium phthalocyanine crystals:

(i) 3 parts of chlorogallium phthalocyamine crystals obtained in step (i) of Synthesis Example 1 was dissolved in 60 parts of a concentrated sulfuric acid at 0° C. The solution was dropwise added to 450 parts of distilled water at 5° C., and the thus precipitated crystals were washed with distilled water and a diluted aqueous ammonia and dried, whereby 2.58 parts of hydroxygallium phthalocyanine crystals were obtained.

(ii) 0.5 part of the hydroxygallium phthalocyanine crystals were ground in an automortar for 5.5 hours, and then milled with 15 parts of dimethylformamide and 30 parts of glass beads (diameter: 1 mm) for 24 hours. After milling, the crystals were separated, washed with methanol and dried to obtain a hydroxygallium phthalocyanine crystal (CG-10) showing distinct diffraction peaks at Bragg angles (2θ±0.2°) of 7.5°, 9.9°, 12.5°, 16.3°, 18.6°, 25.1°, and 28.3°.

(iii) The same treatment as in step (ii) above was repeated except that the grinding step was omitted, whereby a hydroxygallium phthalocyamine crystal (CG-12) showing distinct diffraction peaks at Bragg angles of 7.4°, 9.9°, 25.0°, 26.2°, and 28.2° was obtained.

(iv) The same treatment as in step (iii) above was repeated except for using methylene chloride, dimethylsulfoxide, benzyl alcohol, or ethylene glycol in place of dimethylformamide, whereby a hydroxygallium phthalocyanine crystal (CG-7) showing distinct diffraction peaks at Bragg angles (2θ±0.2°) of 7.7°, 16.5°, 25.1°, and 26.6, a hydroxygallium phthalocyanine crystal (CG-8) showing distinct diffraction peaks at Bragg angles (2θ±0.2°) of 7.9°, 16.5°, 24.4°, and 27.6°, a hydroxygallium phthalocyanine crystal (CG-9) showing distinct diffraction peaks at Bragg angles (2θ±0.2°) of 7.0°, 7.5°, 10.5°, 11.7°, 12.7°, 17.3°, 18.1°, 24.5°, 26.2°, and 27.1°, or a hydroxygallium phthalocyanine crystal (CG-11) showing distinct diffraction peaks at Bragg angles (2θ±0.2°) of 6.8°, 12.8°, 15.8°, and 26.0°, respectively, were obtained.

(iv) The same treatment as in step (ii) above was repeated except that the crystals precipitated from the distilled water were not washed with the diluted aqueous ammonia, and the solvent treatment was conducted using dimethylformamide or ethylene glycol, whereby a hydroxygallimam phthalocyanine crystal (CG-13) showing distinct diffraction peaks at Bragg angles (2θ±0.2°) of 8.2°, 12.4°, 16.5°, and 26.3°, or a hydroxygallium phthalocyanine crystal (CG-14) showing distinct diffraction peaks at Bragg angles (2θ±0.2°) of 6.8°, 12.5°, and 26.4°, respectively, were obtained.

Synthesis Example 4

Synthesis of titanyl phthalocyanine crystals:

(i) To 200 parts of 1-chloronephthalene were added 30 parts of 1,3-diiminoisoindoline and 17 parts of titanium tetrabutoxide, and they were reacted at 190° C. for 5 hours under a nitrogen gas stream. The reaction products were separated by filtration and washed with an aqueous ammonia, water and acetone to thereby 40 parts of titanyl phthalocyanine crystals.

(ii) 5 parts of the thus obtained titanyl phthalocyanine crystals were subjected to a salt milling treatment with 10 parts of sodium chloride in an automortar (LABO-MILL UT-21) for 3 hours. The resultant was thoroughly washed with distilled water and dried to obtain 4.8 parts of titanyl phthalocyanine crystals having a low crystallinity which showed a distinct diffraction peak at Bragg angle (2θ±0.2°) of 27.3. Thereafter, 2 parts of the titanyl phthalocyanine crystals were added to a mixed solvent of 20 parts of distilled water and 2 parts of monochlorobenzene and stirred at 50° C. for 1 hour, followed by filtration. The thus obtained wet cake was thoroughly washed with methanol and dried to obtain a titanyl phthalocyanine hydrate crystal (CG-15) which showed a distinct diffraction peak at Bragg angle (2θ±0.2°) of 27.3. When the hydrate crystal was dried for 8 hours under reduced pressure of 0.1 mmHg and then allowed to stand for 12 hours under atmospheric conditions, the crystal had a structure represented by the formula $TiPc(H_2O)_{0.49}$ (wherein Pc is a phthalocyanine residue) and showed the data of elemental analysis as follows:

C: 65.90%, H: 2.80%, N: 18.70%

(iii) 20 parts of titanyl phthalocyanine obtained in step (i) above was dissolved in 1000 parts of 97% sulfuric acid at 5° C., and the solution was poured into 1300 parts of ice water. The thus precipitated crystals were thoroughly washed with water and dried to obtain titanyl phthalocyanine crystals having a low crystallinity. 0.5 parts of the titanyl phthalocyanine crystals was then milled with 15 parts of ethyl acetate and 30 parts of glass beads (diameter: 1 mm) for 24 hours, whereby a titanyl phthalocyanine crystal (CG-16) showing at least distinct diffraction peaks at Bragg angles (2θ±0.2°) of 9.2°, 13.1°, 20.7°, 26.2°, and 27.1° was obtained.

(iv) The same treatment as in step (iii) above was repeated except for using dimethylformamide in place of ethyl acetate, whereby a titanyl phthalocyanine crystal (CG-17) showing at least distinct diffraction peaks at Bragg angles (2θ±0.2°) of 7.6°, 12.3°, 16.3°, 25.3°, and 28.7° was obtained.

The phthalocyanine compounds as described above are dispersed as a charge generating material in a binder resin of a photosensitive layer. In the aforesaid laminate type photosensitive layer, the phthalocyamine compounds are dispersed in a binder resin of a charge generating layer. The binder resin can be chosen from a wide variety of insulating resins as well as organic photoconductive polymers, such as poly-N-vinylcarbazole, polyvinylanthracene, polyvinylpyrene, and polysilane. Preferred examples of the binder resin include a polyvinylbutyral resin, a polyarylate resin (e.g., a polycondensate of bisphenol and phthalic acid), a polycarbonate resin, a polyester resin, a phenoxy resin, vinyl chloride-vinyl acetate copolymer, a polyamide resin, an acrylic resin, a polyarylamide resin, a polyvinyl-pyridine resin, a cellulose resin, a urethane resin, an epoxy resin, casein, polyvinyl alcohol, and a polyvinylpyrolidone resin. The binder resin may be used independently or as a mixture thereof.

The compounding ratio (weight ratio) of the charge generating material to the binder resin is preferably from 10/1 to 1/10.

The phethalocyanine compounds can be dispersed in the binder resin in a conventional manner using a ball mill, an attritor, a sand mill or the like, but care should be taken so as not to alter the crystal form of phthalocyanine crystals.

The particle size of the phthalocyanine crystals dispersed in the binder resin is generally not more than 0.5 μm, preferably 0.3 μm or less, and particularly preferably 0.15 μm or less.

Organic solvents are used for dispersing the phthalocyanine crystals in the binder resin, and examples thereof include methanol, ethanol, n-propanol, n-butanol, benzyl alcohol, methyl cellosolve, ethyl cellosolve, acetone, methyl ethyl ketone, cyclohexanone, methyl acetate, n-butyl acetate, dioxane, tetrahydrofuran, methylene chloride, chloroform, chlorobenzene, toluene, and the like. They may be used alone, or as admixture thereof.

Charge generating materials which can be used in the electrophotographic photoreceptor of the present invention are not limited to the aforesaid phthalocyanine compounds, and any known charge generating materials can be used with the triarylamine compound represented by formula (I) of the present invention.

The present invention is explained in more detail with reference to the following Examples, wherein all parts are by weight. However, the present invention should not be construed as being limited thereto.

EXAMPLE 1

(1) Synthesis of 3,4-dimethylacetanilide

To 6.6 liters of distilled water was added 240 ml of concentrated hydrochloric acid, and 330 g of 3,4-xylidine was dissolved therein. Then, 278 g of acetic anhydride was added to the solution to, which a solution obtained by dissolving 721 g of sodium acetate trihydrate in 1200 ml of distilled water was added dropwise. After stirring the mixture for 3 hours at room temperature, 6 kg of ice was added thereto, and crystals precipitated were collected, fully washed with water and recrystallized from a mixed solvent of acetone and hexane to provide 362 g of 3,4-dimethylacetylacetanilide. (Melting point 102° to 104° C., colorless crystals)

(2) Synthesis of 3,4,4'-trimethyldiphenylamine

In a 2-liter three-neck flask were placed 120 g of 3,4-dimethylacetanilide, 193 g of p-iodotoluene, 122 g of anhydrous potassium carbonate and 2 g of copper sulfate pentahydrate, and after carrying out the reaction for 30 hours at 200° C. under a nitrogen gas stream, the reaction mixture was cooled to room temperature. To the reaction mixture was added a solution formed by dissolving 120 g of potassium hydroxide in 600 ml of ethanol, and the mixture was refluxed for 1.5 hours. After the reaction was completed, the reaction mixture was cooled to room temperature, thereafter, inorganic salts were removed by filtration, and the solvent was distilled off from the filtrate under reduced pressure. The residual filtrate was subjected to distillation under reduced pressure (not higher than 145° C./0.2 mmHg) and then recrystallized from methanol to provide 121 g of 3,4,4'-trimethyldiphenylamine. (Melting point 62° to 64° C., colorless crystals)

(3) Synthesis of 3,4,4',4''-tetramethylphenylamine (CT-3)

In a one-liter three-neck flask were placed 50 g of 3,4,4'-trimethyldiphenylamine, 62 g of p-iodotoluene, 33 g of anhydrous potassium carbonate, 2 g of copper sulfate petahydrate and 10 ml of n-tridecane, and after carrying out the reaction for 120 hours at 200° C. under a nitrogen gas stream, the reaction mixture was cooled to room temperature. The reaction mixture was subjected to a column purification using a mixed solvent of n-hexane and toluene (volume ratio: 10/1) with activated alumina and the solvent was distilled off under reduced pressure. The residue was recrystallized from a mixed solvent of ethyl acetate and ethanol to provide 52 g of 3,4,4',4''-tetramethyltriphenylamine. (Melting point 107° to 109° C., colorless crystals, IR spectrum shown in FIG. 1.)

EXAMPLE 2

Synthesis of N-(4-methylphenyl)-N-(3,4-dimethylphenyl)-biphenyl-4-amine (CT-4)

Figure 2:
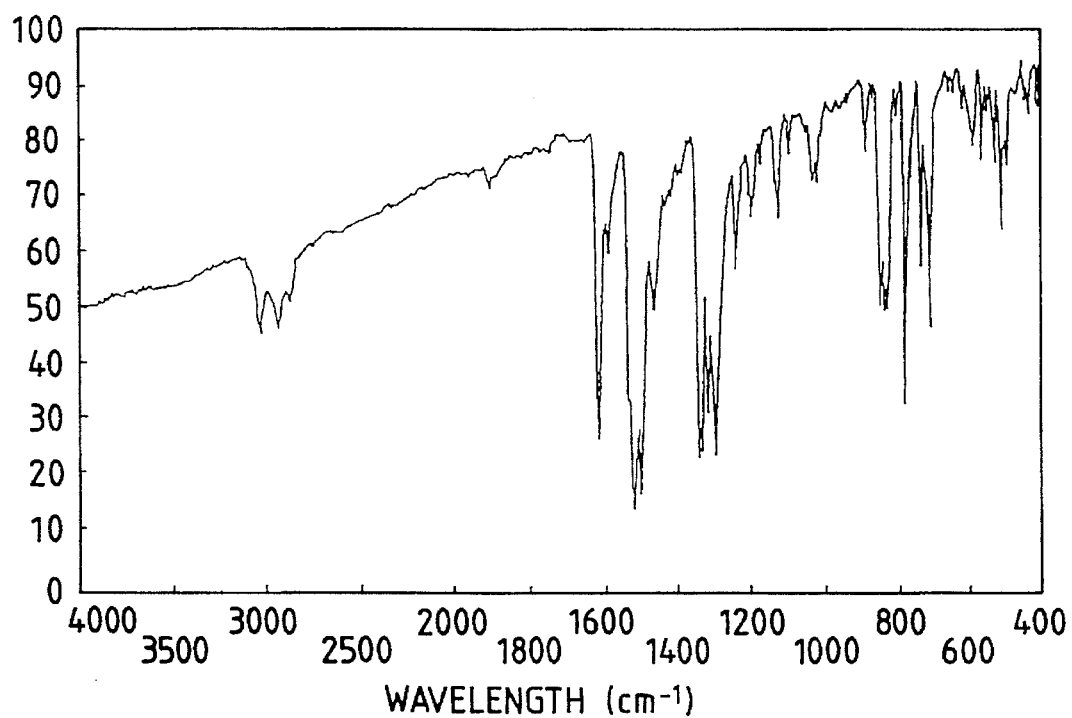

In a 500-ml three-neck flask were placed 20.7 g of 3,4,4'-trimethyldiphenylamine synthesized in Example 1 (2), 25 g of 4-iodobiphenyl, 13 g of anhydrous potassium carbonate, 2 g of copper sulfate pentahydrate and 20 ml of n-tridecane, and after carrying out the reaction for 30 hours at 200° C., the reaction mixture was cooled to room temperature. The reaction mixture was subjected to a column purification (solvent: n-hexane/toluene=10/1) with activated alumina and the solvent was distilled off under reduced pressure. The residue was recrystallized from a mixed solvent of ethyl acetate and ethanol to provide 28 g of N-(4-methylphenyl)-N-(3,4-dimethylphenyl)biphenyl-4-amine. (Melting point 128° to 129.5° C., colorless crystals, IR spectrum shown in FIG. 2.)

EXAMPLE 3

(1) Synthesis of 3,3',4,4'-tetramethyldipenylamine

In a 2-liter three-neck flask were placed 120 g of 3,4-dimethylacetanilide synthesized in Example 1 (1), 253 g of unpurified 4-bromo-o-xylene (purity about 70%, containing about 30% 3-bromo-o-xylene), 122 g of anhydrous potassium carbonate and 2 g of copper sulfate pentahydrate, and after carrying out the reaction for 60 hours at 200° C. under a nitrogen gas stream, the reaction mixture was cooled to room temperature. To the reaction mixture was added a solution obtained by dissolving 120 g of potassium hydroxide in 600 ml of ethanol, and the mixture was refluxed for 4 hours. After the reaction was completed, the reaction mixture was cooled to room temperature, and then, inorganic salts were removed by filtration, and the solvent was distilled off from the filtrate under reduced pressure. The remaining filtrate was recrystallized from methanol under reduced pressure (about 155° C./0.2 mmHg) to provide 117 g of 3,3',4,4'-tetramethyldiphenylamine. (Melting point 80° to 82° C., colorless crystals) (2) Synthesis of 3,3',4,4',4''-pentamethyltriphenylamine (CT-13)

Figure 3:
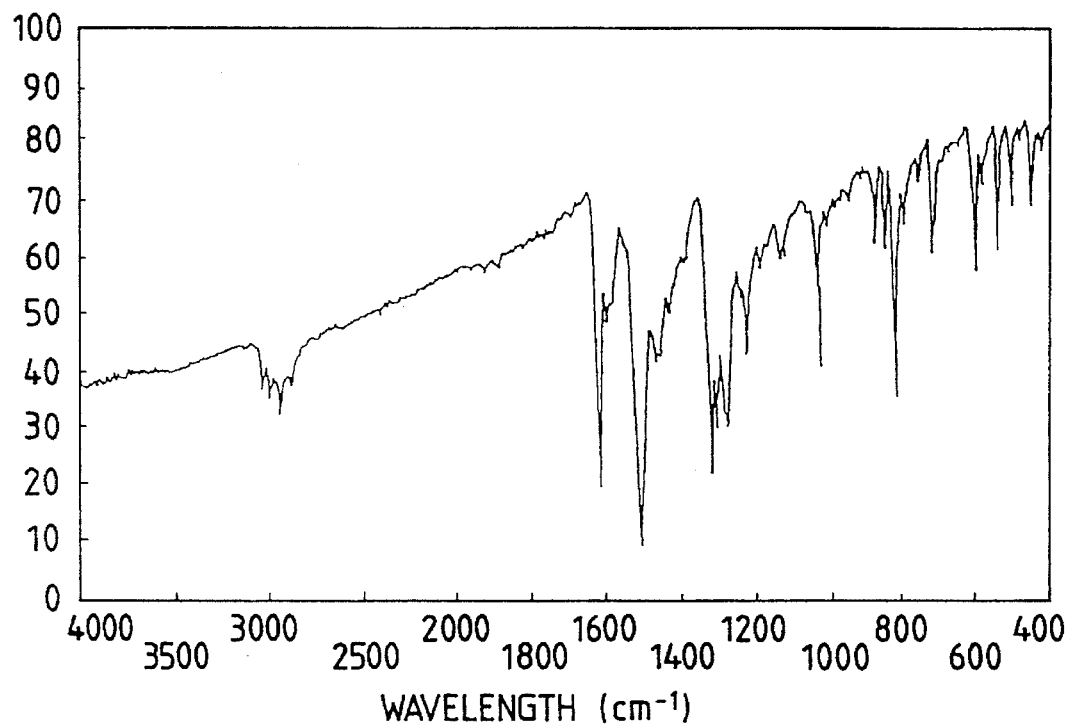

In one-liter three-neck flask were placed 50 g of 3,3',4,4'-tetramethyldiphenylamine, 58 g of p-iodotoluene, 30 g of anhydrous potassium carbonate, 2 g of copper sulfate pentahydrate and 10 ml of n-tridecane, and after carrying out the reaction for 40 hours at 200° C. under a nitrogen gas stream, the reaction mixture was cooled to room temperature. The reaction mixture was subjected to a column purification (solvent: n-hexane/toluene=10/1) with activated alumina and the solvent was distilled off under reduced pressure. The residue was recrystallized from a mixed solvent of ethyl acetate and ethanol to provide 58 g of 3,3',4,4',4''-pentamethyltriphenylamine. (Melting point 115° to 117.5° C., colorless crystals, IR spectrum shown in FIG. 3.)

EXAMPLE 4

Synthesis of N,N-bis(3,4-dimethylphenyl)biphenyl-4-amine (CT-14)

Figure 4:
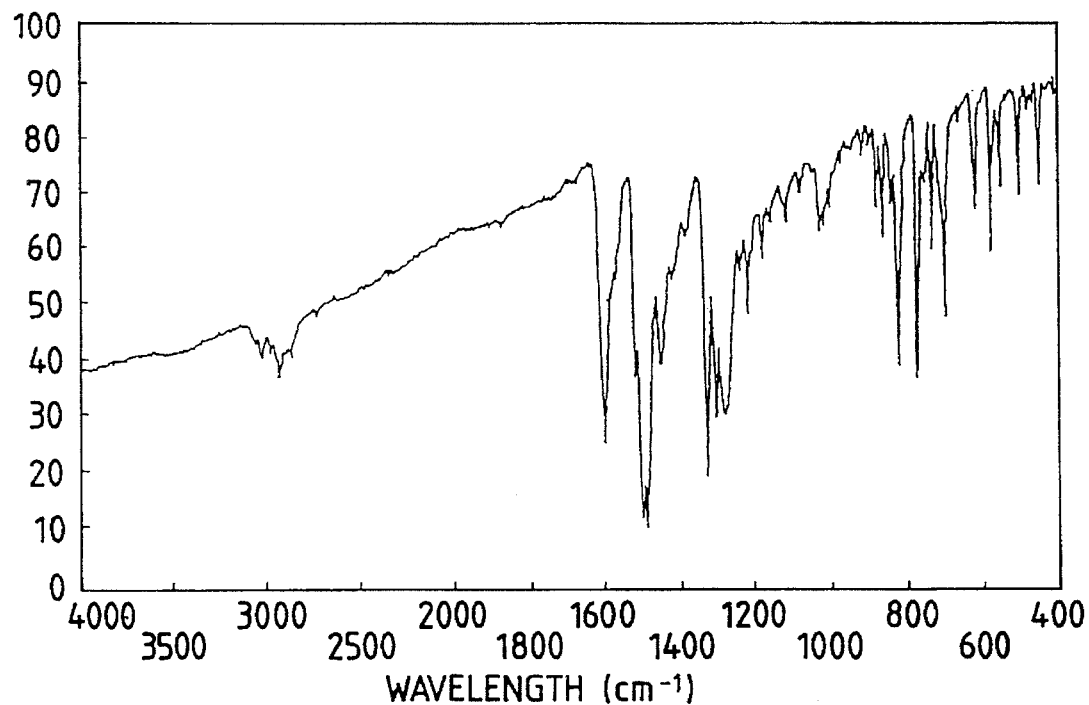

In a 500-ml three-neck flask were placed 31 g of 3,3',4,4'-tetramethyldiphenylamine synthesized in Example 3 (1), 40 g of 4-iodobiphenyl, 19 g of anhydrous potassium carbonate, 2 g of copper sulfate pentahydrate and 20 ml of n-tridecane, and after carrying out the reaction for 28 hours at 200° C. under a nitrogen gas stream, the reaction mixture was cooled to room temperature. The reaction mixture was subjected to a column purification (solvent: n-hexane/toluene =10/1) with activated alumina and the solvent was distilled off under reduced pressure. The residue was recrystallized from a mixed solvent of ethyl acetate and ethanol to provide 37 g of N,N-bis(3,4-dimethylphenyl)biphenyl-4-amine. (Melting point 119° to 120.5° C., colorless crystals, IR spectrum shown in FIG. 4)

EXAMPLE 5

Synthesis of N,N-bis(3,4-dimethylphenyl)naphthalene-1-amine (CT-19)

Figure 5:
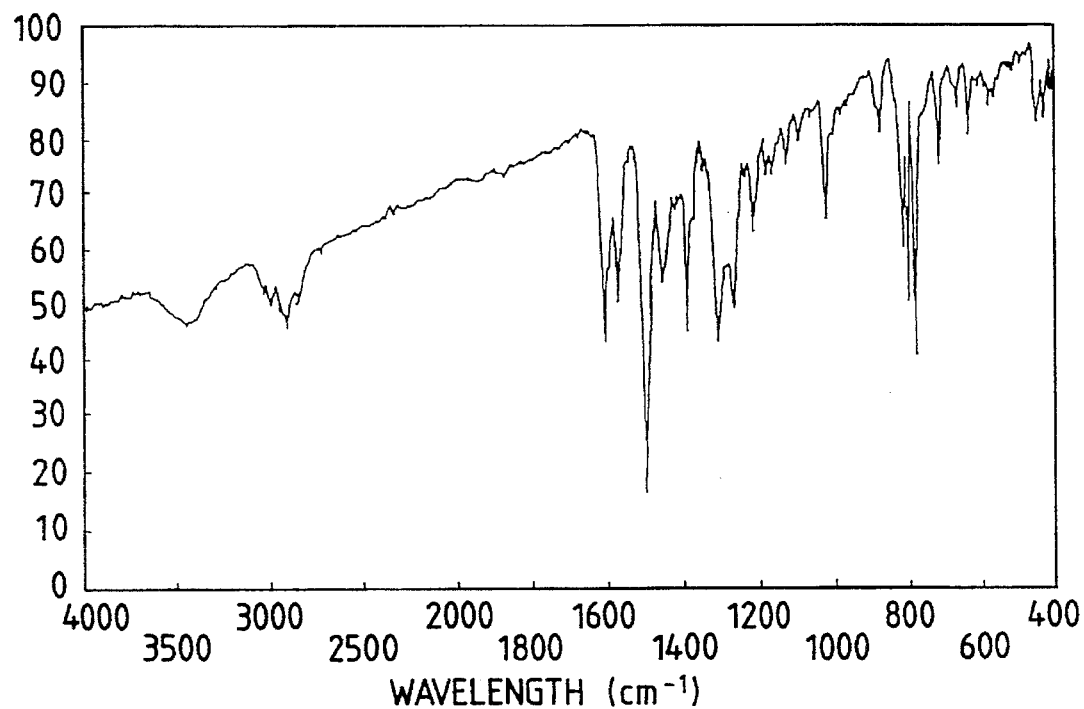

In 100-ml three-neck flask were placed 7.2 g of 3,3',4,4'-tetramethyldiphenylamine synthesized in Example 3 (1), 12.2 g of 1-iodonaphthalene, 5 g of anhydrous potassium carbonate, 0.5 g of copper sulfate pentahydrate and 10 ml of n-tridecane, and after carrying out the reaction for 25 hours at 200° C. under a nitrogen gas atmosphere, the reaction mixture was cooled to room temperature. The reaction mixture was subjected to a column purification (solvent: n-hexane) with activated alumina and the solvent was distilled under reduced pressure. The residue was recrystallized from ethanol to provide 4.2 g of N,N-bis(3,4-dimethylphenyl)naphthalene-1-amine. (Melting point 125° to 127° C., light yellow crystals, IR spectrum shown in FIG. 5.)

EXAMPLE 6

Synthesis of 3,3',3'',4,4',4''-hexamethyltriphenylamine (CT-25)

Figure 6:
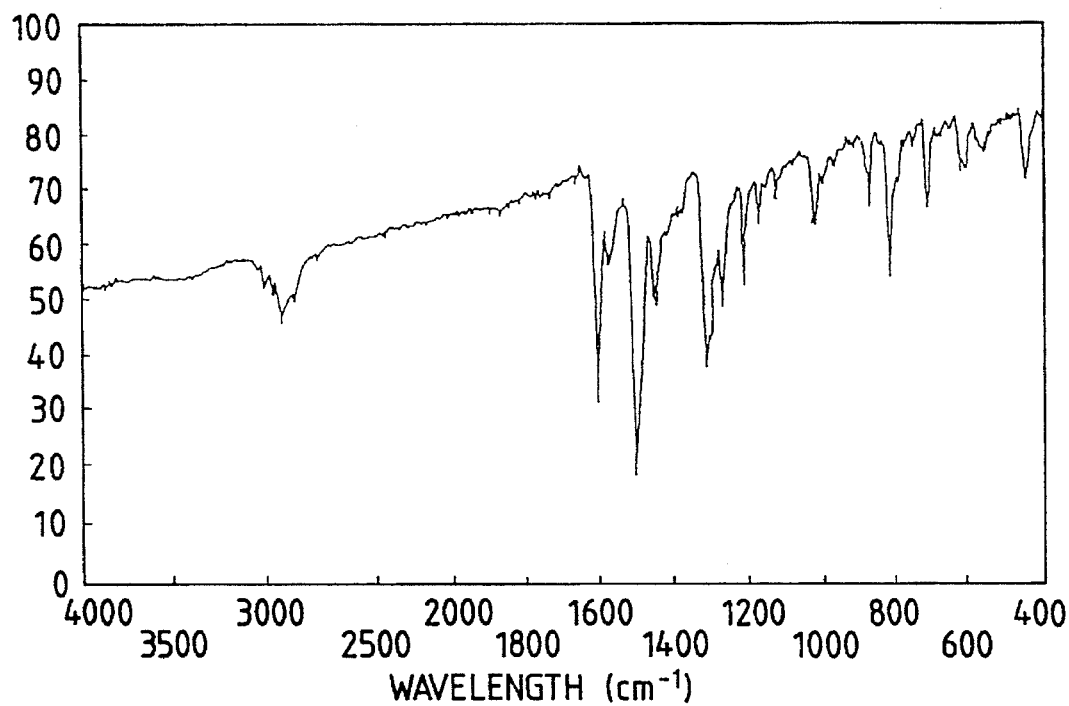
Figure 7:
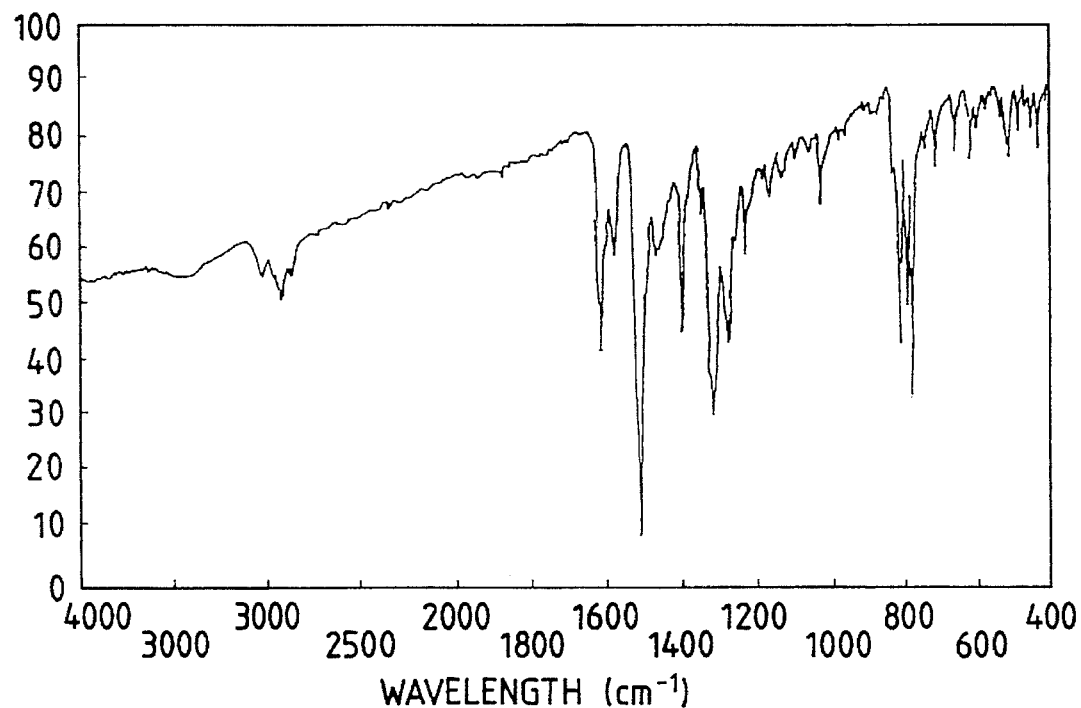
Figure 8:
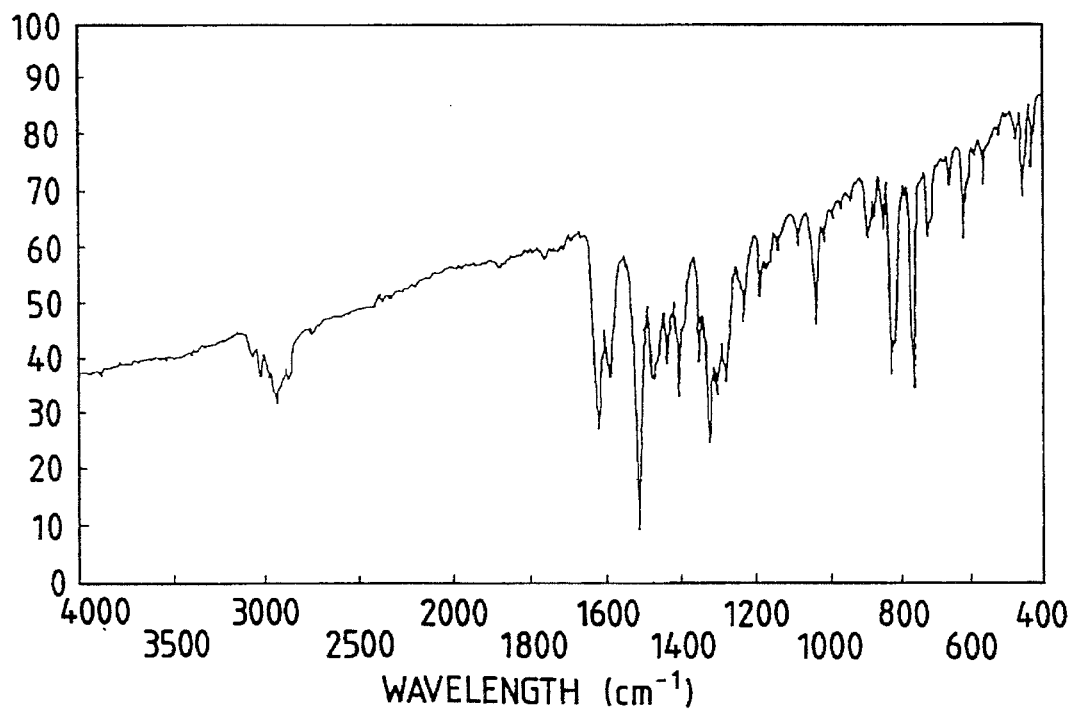
Figure 9:
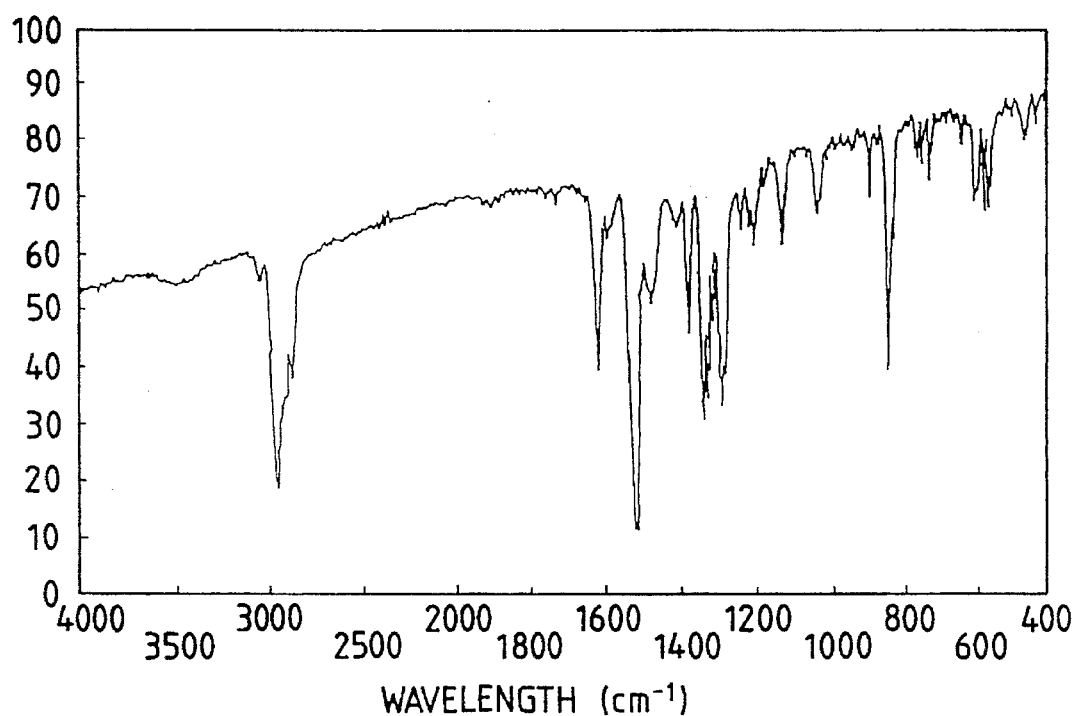
Figure 10:
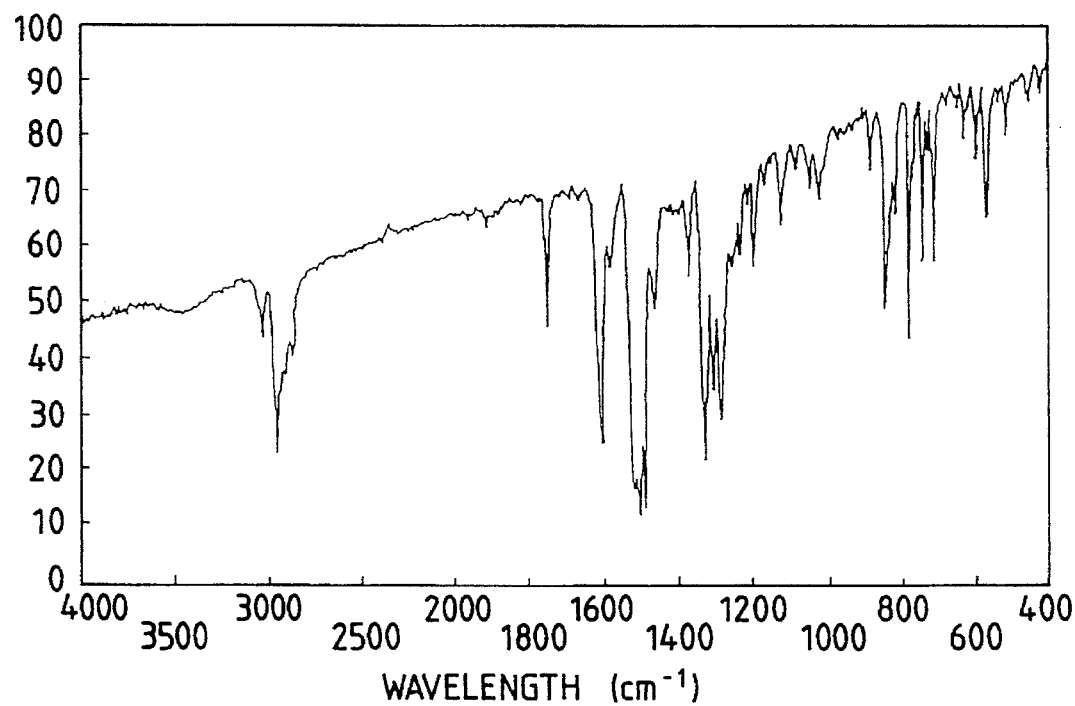
Figure 11:
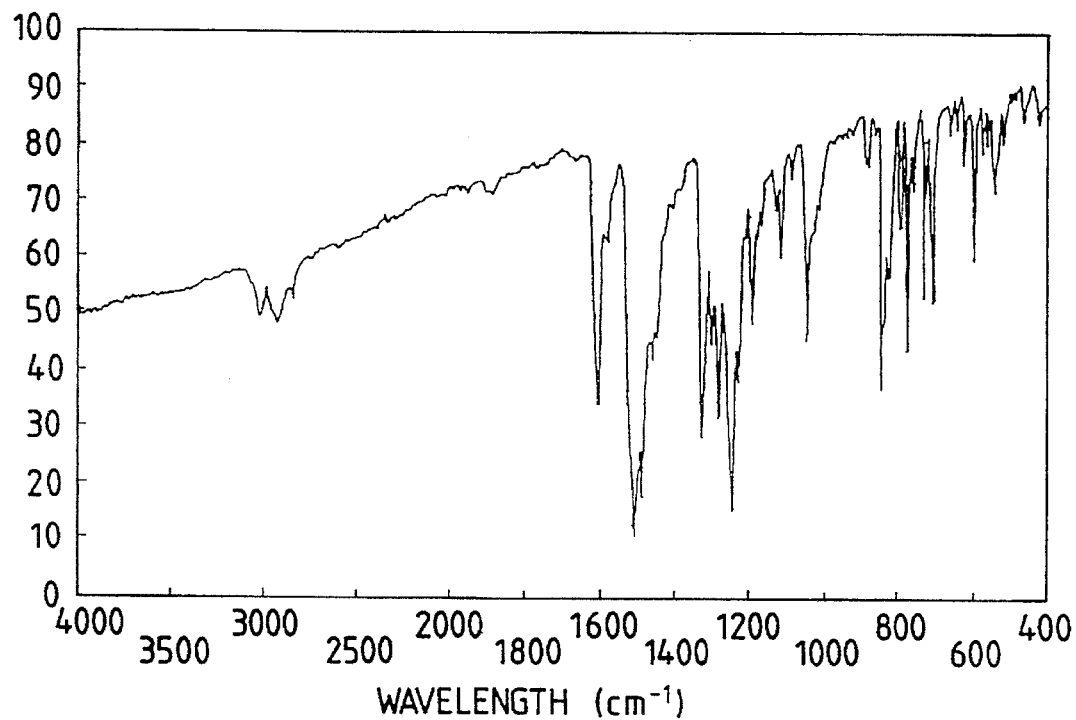
Figure 12:
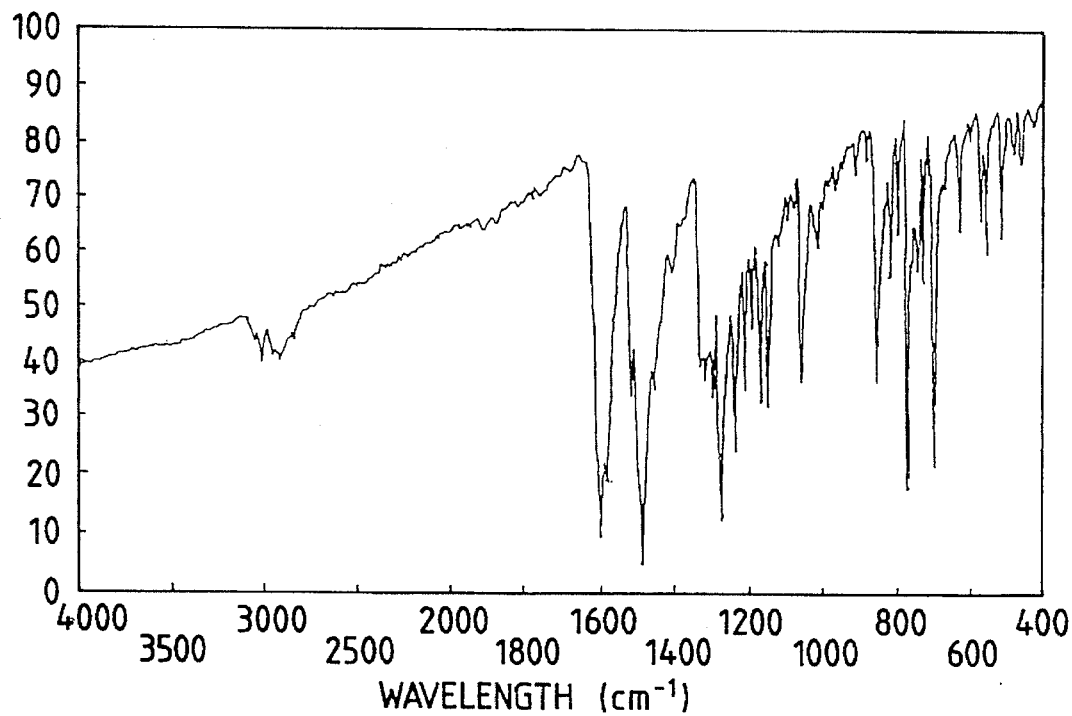
Figure 13:
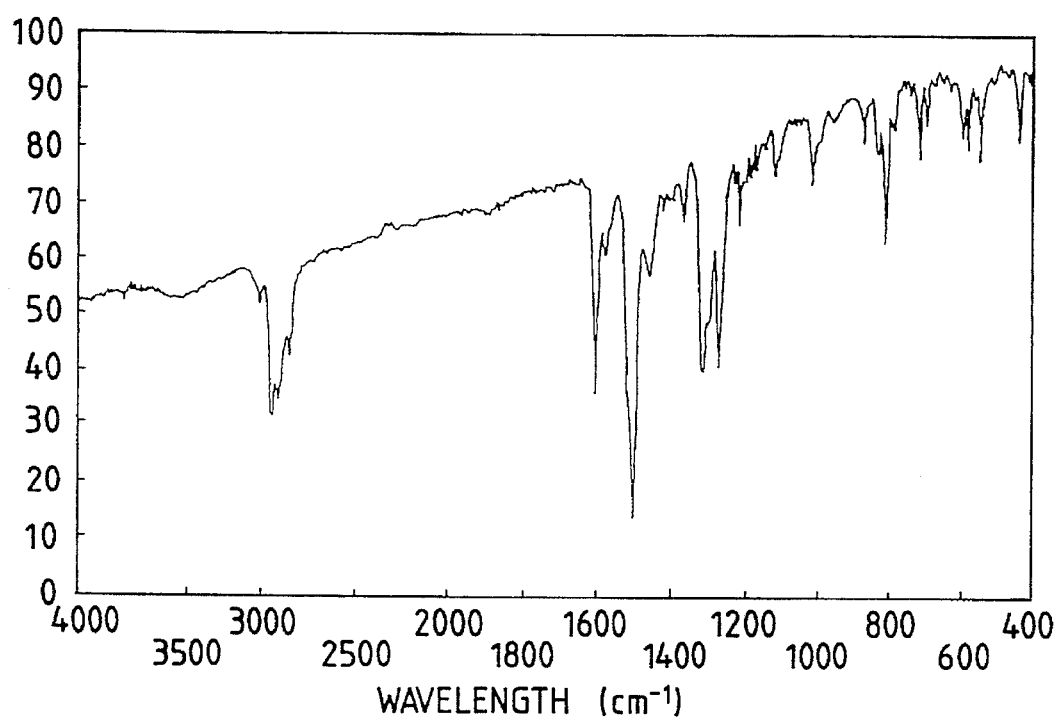
Figure 14:
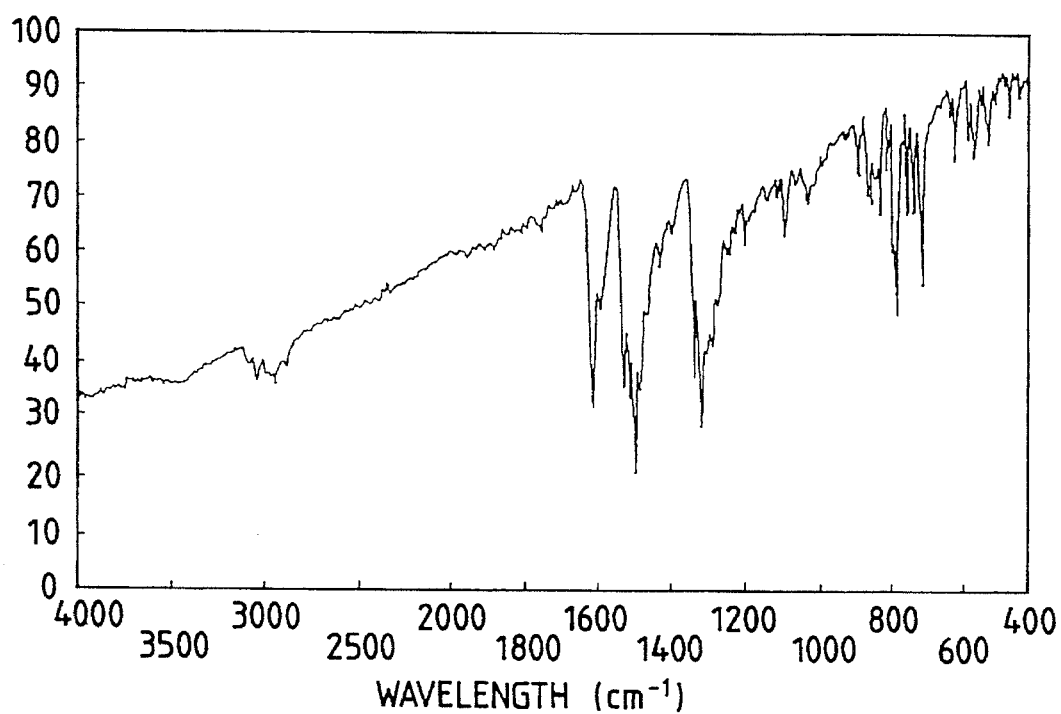

In a one-liter three-neck flask were placed 50 g of 3,3',4,4'-tetramethyldiphenylamine, 70 g of unpurified 4-bromo-o-xylene (purity about 70%, containing about 30% 3-bromo-o-xylene, made by Aldrich Co.), 30 g of anhydrous potassium carbonate, 2 g of copper sulfate pentahydrate, 1 g of iodine and 10 ml of n-tridecane, and after carrying out the reaction for 150 hours at 200° C. under a nitrogen gas atmosphere, the reaction mixture was cooled to room temperature. Then, the unreacted bromoxylene was distilled off from the reaction mixture under reduced pressure. The residue was subjected to a column purification (solvent: n-hexane/toluene=10/1) with activated alumina and the solvent was dsitilled off under reduced pressure. The residue was a mixture of 3,3',3'',4,4',4''-hexamethyltriphenylamine and 2,3,3',3'',4',4''-hexamethyltriphenylamine (molar ratio: 7/1). The residue was recrystallized from a mixed solvent of ethyl acetate and ethanol to provide 30 g of 3,3',3'',4,4',4''-hexamethyltriphenylamine. (Melting point 137° to 139° C., colorless crystals, IR spectrum shown in FIG. 6.)

EXAMPLE 7 TO 14

By following the same procedure as Example 1, the compounds shown in Table 2 were synthesized.

TABLE 2

| Example | Compound No. | Melting Point (°C.) | IR (FIG.) |
|---|---|---|---|
| 7 | CT-9 | 101–103 | 7 |
| 8 | CT-20 | 123–125 | 8 |
| 9 | CT-27 | 98–100 | 9 |
| 10 | CT-28 | 144–146 | 10 |
| 11 | CT-29 | 135.5–137 | 11 |
| 12 | CT-30 | 116.5–117.5 | 12 |
| 13 | CT-31 | 62.5–64.5 | 13 |

TABLE 2-continued

| Example | Compound No. | Melting Point (°C.) | IR (FIG.) |
|---|---|---|---|
| 14 | CT-32 | 140–143 | 14 |

TEST EXAMPLE

Each of the compounds shown in Table 3 described below and a polycarbonate resin were mixed in a weight ratio of 1/1 to form a layer, and the mobility of the compound in the layer was measured by the method described in *Densishashin Gakkai Shi (Journal of Electrophotographic Society).*, Vol. 30, 16(1990).

The mobilities in an electric field intensity of 30 V/μm are shown in Table 3 below.

TABLE 3

| Compound No. | Mobility (cm$^2$/Vsec) |
|---|---|
| CT-13 | $1.7 \times 10^{-5}$ |
| CT-14 | $2.1 \times 10^{-5}$ |
| CT-19 | $1.9 \times 10^{-5}$ |
| CT-25 | $3.9 \times 10^{-5}$ |
| Comparison Compound 1 | $2.8 \times 10^{-6}$ |
| Comparison Compound 2 | $1.3 \times 10^{-6}$ |
| Comparison Compound 3 | $1.0 \times 10^{-5}$ |

(Note):
Comaprison Compound 1: 4,4',4''-Trimethyltriphenylamine
Comparison Compound 2: 2,4,4',4''-Tetramethyltriphenylamine
Comparison Compound 3: N,N-Diphenylbiphenyl-4-amine

EXAMPLE 15

A solution composed of 10 parts of a zirconium compound ("Orgatics ZC540", trade name, made by Matsumoto Seiyaku K.K.), 1 part of a silane compound ("A1110", trade name, made by Nippon Unicar K.K.), 40 parts of i-propanol, and 20 parts of butanol was coated on an aluminum substrate by a dip coating method and heated for 10 minutes at 150° C. to form an underlayer having a thickness of 0.5 μm.

Separately, 1 part of X-type metal free phthalocyanine was mixed with 1 part of a polyvinyl butyral resin ("S-Lex BM-S", trade name, made by Sekisui Chemical Co., Ltd.) and 100 parts of n-butyl acetate. The coating liquid obtained was coated on the foregoing underlayer by a dip coating method and dried by heating for 10 minutes at 100° C. to form a charge generating layer of 0.2 μm in thickness.

Then, 2 parts of the aforesaid Compound CT-3 and 3 parts of a polycarbonate resin having a repeating unit of the following structural formula were dissolved in 20 parts of monochlorobenzene, and the coating liquid obtained was coated on the charge generating layer by a dip coating method and dried by heating for 1 hours at 120° C. to form a charge transport layer of 20 μm in thickness.

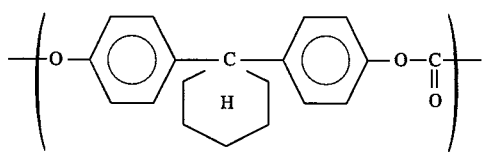

The electrophotographic characteristics of the thus prepared electrophotographic photoreceptor were measured using an electrostatic copying paper test apparatus (Electrostatic Analyzer EPA-8100, trade name, made by Kawaguchi Denki K.K.). That is, the electrophotographic photoreceptor was electrostatically charged by corona dischage of −6 kV at 20° C. and 40% RH using the foregoing electrostatic copying paper test apparatus. The electrophotographic photoreceptor was then exposed to a monochromatic light of 800 n.m. from a tungsten lamp using a monochrometer by controlling such that the exposure amount on the surface of the photoreceptor became 1 μW/cm². Then, the surface potential $V_O$ (volt) and the half decay light-exposure amount $E_{1/2}$ (erg/cm²) were measured. Thereafter, the electrophotographic photoreceptor was exposed to a white light of 10 lux for one second, and the residual potential $V_{RP}$ (volt) was measured. Furthermore, after repeating the above charging-and-exposing procedure 1,000 times, $V_O$, $E_{1/2}$, and $V_{RP}$ and the changes thereof ($^\Delta V_O$, $^\Delta E_{1/2}$, and $^\Delta V_{RP}$) from those measured at the beginning were measured, and the results are shown in Table 4 below.

EXAMPLES 16 TO 28

By following the same procedure as in Example 15 except that each of the compounds shown in Table 4 below was used as a charge transport material in place of Compound CT-3, elecrophotographic photoreceptors were prepared and the electrophotographic characteristics were evaluated. The results obtained are shown in Table 4 below.

COMPARATIVE EXAMPLES 1 TO 3

By following the same procedure as in Example 15 except that each of 4,4',4"-trimethyltriphenylamine (Comp. CT-1), 4-ethyl-4',4"-dimethyltriphenylamine (Comp. CT-2), and N,N-diphenyl-biphenyl-4-amine (Comp. CT-3) was used in place of Compound CT-3, electrophotographic photoreceptors were prepared and the characteristics were measured in the same manner as above.

The results are shown in Table 4 below.

TABLE 4

| Example No. | Charge Transport Material | 1st Running $V_O$ (V) | 1st Running E½ (erg/cm²) | 1st Running $V_{RP}$ (V) | 1000th Running $V_O$ (V) | 1000th Running E½ (erg/cm²) | 1000th Running $V_{RP}$ (V) | Stability ΔE½ (erg/cm²) | Durability Δ$V_O$ (V) | Durability Δ$V_{RP}$ (V) |
|---|---|---|---|---|---|---|---|---|---|---|
| 15 | CT-3 | −822 | 6.9 | −55 | −801 | 7.6 | −79 | 0.7 | 21 | 24 |
| 16 | CT-4 | −818 | 6.9 | −56 | −801 | 7.4 | −72 | 0.5 | 17 | 16 |
| 17 | CT-13 | −814 | 6.8 | −51 | −795 | 7.3 | −73 | 0.5 | 19 | 22 |
| 18 | CT-14 | −817 | 6.9 | −54 | −799 | 7.4 | −70 | 0.5 | 18 | 16 |
| 19 | CT-19 | −821 | 6.9 | −57 | −806 | 7.4 | −75 | 0.5 | 15 | 18 |
| 20 | CT-25 | −809 | 6.8 | −45 | −795 | 7.3 | −62 | 0.5 | 14 | 17 |
| 21 | CT-9 | −820 | 6.9 | −60 | −803 | 7.4 | −79 | 0.5 | 17 | 19 |
| 22 | CT-20 | −817 | 6.9 | −55 | −801 | 7.4 | −72 | 0.5 | 16 | 17 |
| 23 | CT-27 | −825 | 6.9 | −59 | −807 | 7.5 | −79 | 0.6 | 18 | 20 |
| 24 | CT-28 | −820 | 6.9 | −59 | −804 | 7.4 | −75 | 0.5 | 16 | 16 |
| 25 | CT-29 | −823 | 6.9 | −60 | −803 | 7.5 | −81 | 0.6 | 20 | 21 |
| 26 | CT-30 | −801 | 6.8 | −50 | −787 | 7.3 | −68 | 0.5 | 14 | 18 |
| 27 | CT-31 | −830 | 7.0 | −65 | −812 | 7.5 | −86 | 0.5 | 18 | 21 |
| 28 | CT-32 | −821 | 6.9 | −62 | −802 | 7.4 | −79 | 0.5 | 19 | 17 |
| Comp. Ex. 1 | 4,4',4"-Trimethyltriphenylamine | −830 | 6.9 | −59 | −807 | 7.7 | −85 | 0.8 | 23 | 26 |
| Comp. Ex. 2 | 4-Ethyl-4',4"-dimethyltriphenyl amine | -831 | 6.9 | −61 | −818 | 8.0 | −98 | 1.1 | 13 | 37 |
| Comp. Ex. 3 | N,N-Diphenyl-biphenyl-4-amine | −845 | 7.1 | −72 | -820 | 8.1 | −115 | 1.0 | 25 | 43 |

EXAMPLES 29 TO 56

By following the same procedure as in Example 15 except that each of the charge generating materials shown in Table 5 was used in place of the X-type metal free phthalocyanine and each of the charge transport material shown in Table 5 was used in place of Compound CT-3, electrophotographic photoreceptors were prepared and the electrophotographic characteristics were evaluated. The results obtained are shown in Table 5 below.

COMPARATIVE EXAMPLES 4 TO 15

By following the same procedure as in Example 29 except that the charge generating marerial and the charge transport materials were changed to those shown in Table 5, electrophotographic photoreceptors were prepared and the characteristics were measured in the same manner as above.

The results are shown in Table 5 below.

TABLE 5

| | Charge Transport Material | Charge Generating Material | 1st Running | | | 1000th Running | | | Stability | Durability | |
|---|---|---|---|---|---|---|---|---|---|---|---|
| | | | $V_O$ (V) | E½ (erg/cm$^2$) | $V_{RP}$ (V) | $V_O$ (V) | E½ (erg/cm$^2$) | $V_{RP}$ (V) | ΔE½ (erg/cm$^2$) | Δ$V_O$ (V) | Δ$V_{RP}$ (V) |
| Example | | | | | | | | | | | |
| 29 | CT-4 | CG-1 | −819 | 2.4 | −14 | −805 | 2.8 | −22 | 0.4 | 14 | 8 |
| 30 | CT-14 | CG-1 | −817 | 2.4 | −13 | −806 | 2.8 | −20 | 0.4 | 13 | 7 |
| 31 | CT-19 | CG-1 | −825 | 2.4 | −18 | −812 | 2.8 | −27 | 0.4 | 11 | 9 |
| 32 | CT-25 | CG-1 | −814 | 2.4 | −11 | −801 | 2.8 | −20 | 0.4 | 13 | 9 |
| 33 | CT-31 | CG-2 | −823 | 2.8 | −14 | −811 | 3.0 | −22 | 0.2 | 12 | 8 |
| 34 | CT-31 | CG-3 | −819 | 2.7 | −18 | −805 | 3.0 | −26 | 0.3 | 14 | 8 |
| 35 | CT-3 | CG-4 | −827 | 2.7 | −10 | −813 | 3.0 | −19 | 0.3 | 14 | 9 |
| 36 | CT-13 | CG-4 | −824 | 2.7 | −8 | −812 | 2.9 | −17 | 0.2 | 12 | 9 |
| 37 | CT-6 | CG-5 | −850 | 2.6 | −14 | −836 | 2.8 | −22 | 0.2 | 14 | 8 |
| 38 | CT-27 | CG-6 | −845 | 3.3 | −19 | −830 | 3.5 | −27 | 0.2 | 15 | 8 |
| 39 | CT-34 | CG-6 | −844 | 3.3 | −17 | −830 | 3.6 | −26 | 0.3 | 14 | 9 |
| 40 | CT-4 | CG-7 | −830 | 2.5 | −32 | −814 | 2.7 | −43 | 0.2 | 16 | 11 |
| 41 | CT-7 | CG-8 | −819 | 2.5 | −34 | −803 | 2.7 | −46 | 0.2 | 16 | 12 |
| 42 | CT-8 | CG-9 | −835 | 3.4 | −38 | −821 | 3.6 | −49 | 0.2 | 14 | 11 |
| 43 | CT-3 | CG-10 | −825 | 2.1 | −25 | −811 | 2.4 | −37 | 0.3 | 14 | 12 |
| 44 | CT-4 | CG-10 | −824 | 2.1 | −23 | −809 | 2.3 | −34 | 0.2 | 15 | 11 |
| 45 | CT-14 | CG-10 | −819 | 2.1 | −21 | −806 | 2.3 | −30 | 0.2 | 13 | 9 |
| 46 | CT-19 | CG-10 | −830 | 2.1 | −31 | −815 | 2.3 | −40 | 0.2 | 15 | 9 |
| 47 | CT-21 | CG-11 | −844 | 2.8 | −37 | −830 | 3.0 | −49 | 0.2 | 14 | 12 |
| 48 | CT-24 | CG-12 | −845 | 2.2 | −39 | −834 | 2.5 | −52 | 0.3 | 11 | 13 |
| 49 | CT-14 | CG-13 | −830 | 2.9 | −25 | −816 | 3.3 | −36 | 0.4 | 14 | 11 |
| 50 | CT-25 | CG-13 | −825 | 2.9 | −20 | −810 | 3.3 | −33 | 0.4 | 15 | 13 |
| 51 | CT-17 | CG-14 | −840 | 4.1 | −43 | −828 | 4.4 | −59 | 0.3 | 12 | 16 |
| 52 | CT-4 | CG-15 | −825 | 1.2 | −10 | −816 | 1.4 | −17 | 0.2 | 9 | 7 |
| 53 | CT-14 | CG-15 | −823 | 1.2 | −13 | −812 | 1.4 | −21 | 0.2 | 11 | 8 |
| 54 | CT-25 | CG-15 | −814 | 1.2 | −7 | −801 | 1.4 | −17 | 0.2 | 13 | 10 |
| 55 | CT-14 | CG-16 | −825 | 1.3 | −43 | −813 | 4.7 | −57 | 0.4 | 12 | 14 |
| 56 | CT-14 | CG-17 | −812 | 2.5 | −31 | −794 | 3.0 | −53 | 0.5 | 18 | 18 |
| Comparative Example | | | | | | | | | | | |
| 4 | Comp. CT-1 | CG-1 | −823 | 2.4 | −15 | −801 | 2.9 | −30 | 0.5 | 22 | 15 |
| 5 | Comp. CT-2 | CG-1 | −825 | 2.4 | −17 | −805 | 3.0 | −34 | 0.6 | 20 | 17 |
| 6 | Comp. CT-2 | CG-4 | −824 | 2.7 | −11 | −803 | 3.2 | −25 | 0.5 | 21 | 14 |
| 7 | Comp. CT-3 | CG-4 | −845 | 2.7 | −14 | −322 | 3.1 | −30 | 0.4 | 23 | 16 |
| 8 | Comp. CT-3 | CG-6 | −855 | 3.3 | −23 | −830 | 3.7 | −40 | 0.4 | 25 | 17 |
| 9 | Comp. CT-3 | CC-10 | −825 | 2.8 | −48 | −802 | 3.2 | −70 | 0.4 | 23 | 22 |
| 10 | Comp. CT-1 | CG-13 | −829 | 2.9 | −23 | −805 | 3.6 | −47 | 0.7 | 24 | 24 |
| 11 | Comp. CT-2 | CG-13 | −827 | 2.9 | −23 | −803 | 3.5 | −50 | 0.6 | 24 | 27 |
| 12 | Comp. CT-2 | CG-15 | −827 | 1.2 | −17 | −802 | 1.5 | −34 | 0.3 | 25 | 17 |
| 13 | Comp. CT-3 | CG-15 | −839 | 1.2 | −20 | −810 | 1.6 | −36 | 0.4 | 29 | 16 |
| 14 | Comp. CT-1 | *I-H$_2$ Pc | −830 | 6.9 | −59 | −807 | 7.7 | −85 | 0.8 | 23 | 26 |
| 15 | Comp. CT-2 | *I-H$_2$ Pc | −831 | 6.9 | −61 | −818 | 8.0 | −98 | 1.1 | 13 | 37 |

Note:
*X-type metal free phthalocyanine

While the invention has been described in detail and with reference to specific embodiments thereof, it will be apparent to one skilled in the art that various changes and modifications can be made therein without departing from the spirit and scope thereof.

What is claimed is:

1. A triarylamine compound represented by formula (I)

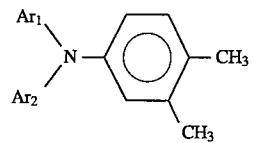

wherein, $Ar_1$ and $Ar_2$ each represents a phenyl group, a phenyl group substituted with an alkyl group having 1–5 carbon atoms or an alkoxy group having 1–5 carbon atoms or a condensed ring group that is a naphthyl group, an anthracenyl group, a pyrenyl group, a fluorenyl group or any of a naphthyl group, an anthracenyl group, a pyrenyl group, or a fluorenyl group substituted with an alkyl group having 1–5 carbon atoms.

2. The triarylamine compound as in claim 1, wherein $Ar_1$ is a 3,4-dimethylphenyl group.

3. The triarylamine compound as in claim 1, wherein $Ar_1$ and $Ar_2$ both are a 3,4-dimethylphenyl group.

4. A process of producing a triaryl amine compound represented by formula (I)

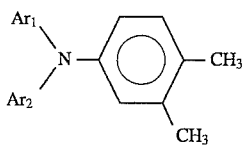

wherein $Ar_1$ and $Ar_2$ each represents a phenyl group, a phenyl group substituted with an alkyl group having 1 to 5 carbon atoms or an alkoxy group having 1–5 carbon atoms or a condensed ring group that is a naphthyl group, an anthracenyl group, a pyrenyl group, a fluorenyl group or any of a naphthyl group, an anthracenyl group, a pyrenyl group, or a fluorenyl group substituted with an alkyl group having 1–5 carbon atoms, which comprises acetylating an amino compound represented by the Formula $Ar_1$-$NH_2$, carrying out a condensation reaction of the acetylated amino compound with a mixture of 3-bromo-o-xylene and 4-bromo-o-xylene to form a diarylamine compound represented by Formula (II)

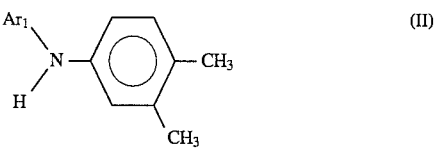

and then carrying out a condensation reaction of the diarylamine compound with a halogenated aryl compound represented by the formula $Ar_2$-$X_1$, wherein $X_1$ represents a bromine atom or an iodine atom.

5. A triarylamine compound represented by formula

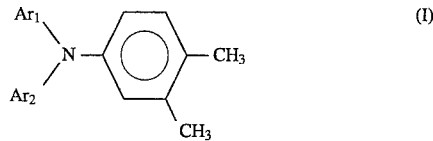

wherein, $Ar_1$ represents a phenyl group substituted with at least a phenyl group or substituted with a phenyl group substituted with an alkyl group having 1 to 5 carbon atoms or with an alkoxy group having 1–5 carbon atoms and $Ar_2$ represents a phenyl group substituted with an alkyl group having 3–5 carbon atoms or an alkoxy group having 1–5 carbon atoms.

* * * * *